United States Patent
Matsumoto (10) Patent No.: US 6,925,144 B2
(45) Date of Patent: Aug. 2, 2005

(54) X-RAY DIGITAL TOMOGRAPHIC IMAGE TAKING APPARATUS

(75) Inventor: Kazuhiro Matsumoto, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 70 days.

(21) Appl. No.: 10/716,148

(22) Filed: Nov. 17, 2003

(65) Prior Publication Data

US 2004/0101093 A1 May 27, 2004

(30) Foreign Application Priority Data

Nov. 26, 2002  (JP) ........................................ 2002-342772

(51) Int. Cl.⁷ .............................................. H05G 1/60
(52) U.S. Cl. ........................... 378/22; 378/39; 378/98.9
(58) Field of Search .............................. 378/21, 22, 4, 378/11, 19, 98.8, 98.9, 98.11, 98.12, 5, 23, 39, 108, 197

(56) References Cited

U.S. PATENT DOCUMENTS

| | | | |
|---|---|---|---|
| 5,715,820 A | * | 2/1998 | Stein et al. .................. 600/407 |
| RE36,162 E | * | 3/1999 | Bisek et al. ................. 378/146 |
| 6,102,567 A | * | 8/2000 | Cabral et al. ................ 378/197 |
| 6,496,557 B2 | * | 12/2002 | Wilson et al. ................. 378/21 |

FOREIGN PATENT DOCUMENTS

JP          2871053 A      3/1999

* cited by examiner

Primary Examiner—Edward J. Glick
Assistant Examiner—Irakli Kiknadze
(74) Attorney, Agent, or Firm—Morgan & Finnegan, L.L.P.

(57) ABSTRACT

An X-ray digital tomographic image taking apparatus which divides the course from the start to end of tomographic image taking into a plurality of sections differing in quality of irradiated X-rays and creates a plurality of tomographic images from the image data differing in quality of X-rays. It also calculates a subtraction image from the plurality of tomographic images.

7 Claims, 6 Drawing Sheets

X-RAY DIGITAL TOMOGRAPHIC IMAGE TAKING APPARATUS

BACKGROUND OF THE INVENTION

1. Field of the Invention

The present invention relates to an X-ray digital tomographic image taking apparatus which visualizes a tomographic image of a subject based on X-rays that have passed through the subject.

2. Relate Background Art

An X-ray tomographic image taking method using an X-ray film is being conventionally practiced. This X-ray tomographic image taking method irradiates a subject with X-ray a plurality of times while moving an X-ray tube and X-ray film synchronously in the directions opposite to each other with respect to the subject placed between them in such a way that the center of the X-ray beam aligns with the center of the X-ray film, in order to multiple expose the respective X-ray transmitted images on a single film and thereby obtain a tomographic image with blurred images of components other than those located in the vicinity of the tomographic image of the subject. Furthermore, a digital tomographic image taking apparatus has also been commercialized which obtains digital image data using an I.I. (image intensifier) instead of an X-ray film and a TV image pickup system and there reconstructs the image by adding up the data to thereby obtain the identical tomographic image as an image of multiple exposed images on a film.

On the other hand, a dual energy subtraction method is known which assigns weights to images obtained with high energy X-rays and low energy X-rays, and subtracts one from the other to extract only bones or calcification diseases, or only soft tissues by erasing bones.

Some known conventional examples in which this dual energy subtraction image taking method is applied to the above described tomographic image taking method include a method of using an imaging plate to take images in two stages; one with high energy and the other with low energy, a method of sandwiching one Cu plate between two imaging plates and obtaining one image with high energy and an image with low energy for each imaging plate simultaneously, as well as a method described in Japanese Patent Registration No. 2871053 of alternating a tube voltage for X-rays irradiated onto an X-ray image taking apparatus, which combines an I.I. and a TV camera, between a high voltage and low voltage for every exposure, or a method of obtaining a high voltage image and low voltage image by replacing X-ray filters to change X-ray energy.

However, the method of performing image taking twice, causes a time interval between two image takings because a high voltage tomographic image is taken first and then a low voltage tomographic image is taken. If the body of the subject moves due to respiration, etc., in this time interval, a position shift occurs between the X-ray images recorded in both taken images, which poses a disadvantage that an accurate difference image cannot be obtained in the dual energy subtraction processing.

The method of using two imaging plates, in which two images with different energy levels can be obtained in one image taking, and so there is no need to take images twice, does not cause an inconvenience due to wobbling of the body of the subject. However, since the two images have not been obtained by switching the tube voltage value of the X-ray tube between high and low, an image produced under the influence of high energy X-rays may appear on the first imaging plate or the second imaging plate may be influenced by low energy X-rays that have passed through the copper plate. Therefore, compared to the method of taking images by switching between tube voltages, the method suffers from a disadvantage that good subtraction images cannot be obtained.

The method of switching the tube voltages or filters alternately for every exposure has the following disadvantages.

A switching time is required, which increases the time required for tomographic image taking and reduces the diagnosis efficiency. Frequent switching of the tube voltage in a short time period increases load on the X-ray tube and reduces its service life. The switching between filters in a short time in synchronization with exposure to X-rays requires an apparatus capable of accurate switching. The same number of calculations as X-ray exposures are required to reconstruct high voltage tomographic images and low voltage tomographic images.

SUMMARY OF THE INVENTION

Considering the actual situation of the above described conventional technologies, there is a demand for an X-ray digital tomographic image taking apparatus capable of dual energy image taking by single tomographic image taking.

According to the present invention, the foregoing object is attained by providing an X-ray digital tomographic image taking apparatus including: an X-ray generation unit for emitting X-rays; a first transfer unit for changing the emission direction of X-rays emitted by the X-ray generation unit and transferring the X-ray generation unit; a solid state image sensing unit consisting of a plurality of solid state image sensing elements for converting X-rays to electric signals; a second transfer unit for transferring the solid state image sensing unit; and a control unit for controlling the first transfer unit and second transfer unit so that X-rays emitted from the X-ray generation unit are emitted to predetermined coordinates on the photoreceiving surface of the solid state image sensing unit, and controlling the emissions of the X-ray generation unit and the drive of the solid state image sensing unit, wherein the control unit divides the course along which the X-ray generation unit or solid state image sensing unit is moving into a plurality of sections and controls the X-ray generation unit so that the quality of the X-rays differs between neighboring sections.

Other features and advantages of the present invention will be apparent from the following descriptions taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

DETAILED DESCRIPTION OF THE PREFERRED EMBODIMENTS

A preferred embodiment of the present invention will be described in detail in accordance with the accompanying drawings.

With reference now to the attached drawings, preferred embodiments of the present invention will be explained in detail below.

Figure 1:
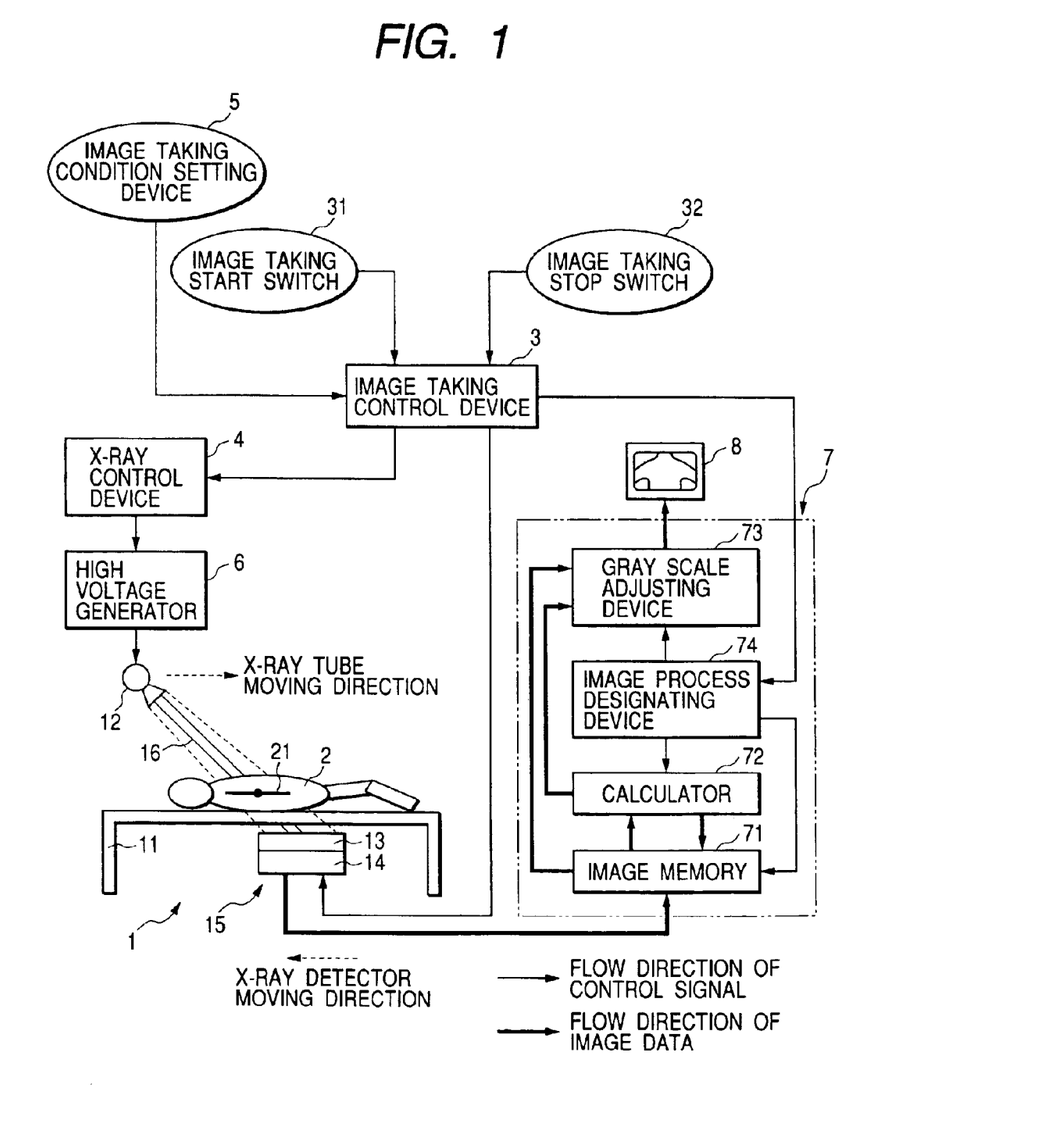
FIG. 1 is a block diagram showing a schematic configuration of an embodiment of an X-ray digital tomographic image taking apparatus according to the present invention.

FIG. 1 is a block diagram showing a schematic configuration of an embodiment of an X-ray digital tomographic image taking apparatus according to the present invention. Reference numeral 1 denotes a tomographic image taking stand, which consists of a bed 11 on which a subject 2 is placed, an X-ray tube 12 placed facing the bed 11 with the subject 2 located in between and an X-ray detector 15 which is made up of a solid state image sensing section 13 accommodated in a housing (not shown) and an image taking drive section 14 which reads the drive of the solid state image sensing section 13 and the X-ray image of the subject as electric signals and generates digital image data. Furthermore, the X-ray tube 12 and the X-ray detector 15 are connected by means of a swing lever 16 in such a way that they move in parallel in directions opposite to each other centered on one point on a tomographic surface 21.

Reference numeral 3 denotes an image taking control device which sends a command to the tomographic image taking stand 1 and an X-ray control device 4 to control a series of processes of tomographic image taking and is connected to an image taking start switch 31 and an image taking stop switch 32 and controls, for example, the movements of the X-ray tube 12 and X-ray detector 15 during image taking and timings of reading an X-ray exposure signal and image data to be sent to the X-ray control device 4 and the image taking drive section 14. Reference numeral 5 denotes an image taking condition setting device, which is connected to the image taking control device 3. The X-ray control device 4 controls a high voltage generator 6 based on the set image taking condition and the X-ray tube 12 irradiates X-rays of a desired tube voltage, tube current and irradiation time. Furthermore, the movements of the X-ray tube 12 and X-ray detector 15 controlled by the image taking control device 3 are also carried out based on the image taking condition set by the image taking condition setting device 5.

Figure 2:
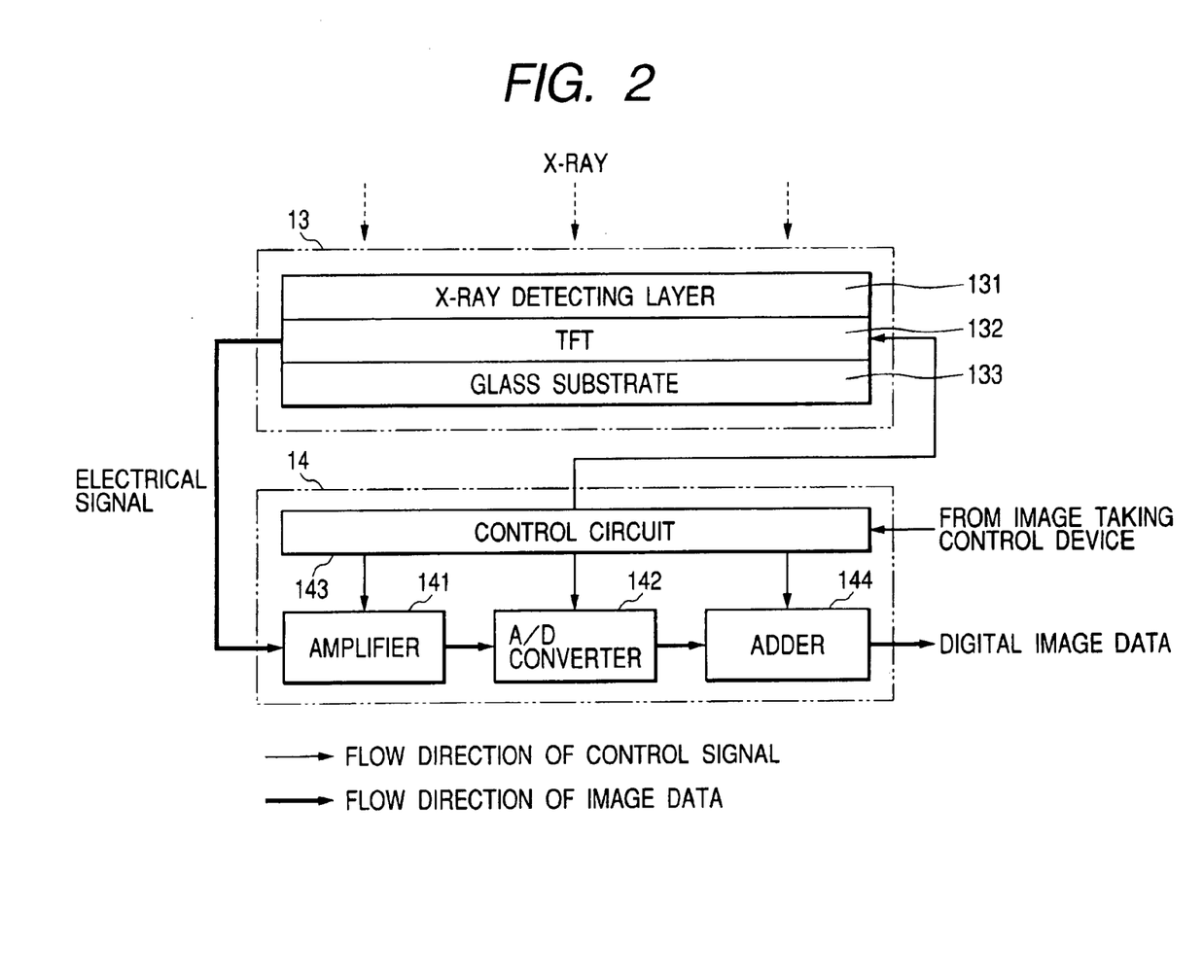
FIG. 2 is a schematic view of a configuration of an X-ray detector.

The solid state image sensing section 13 has a two-dimensional planar shape and is formed, as shown in FIG. 2, of an X-ray detecting layer 131 which converts X-rays that have passed through the subject to electric charge and a matrix-shaped TFT transistor circuit 132 which reads this electric charge and converts it to an electric signal and is formed on a glass substrate 133. Furthermore, the image taking drive device 14 consists of an amplifier 141 which amplifies the electric signal converted by the TFT transistor circuit 132, an A/D converter 142 which converts the output of the amplifier 141 to a digital signal, a control circuit 143, an adder 144 which adds a frame number, etc., to the digital signal controlled by the control circuit 143 and converted by the A/D converter 142 and outputs digital image data. The control circuit 143 controls drive timings for reading the electric charge converted from X-rays by the X-ray detecting layer 131 by the TFT transistor circuit 132 as an electric signal, the A/D converter 142 and adder 144 and also the gain setting for the amplifier 141. This image taking drive section 14 and the solid state image sensing section 13 are accommodated in the housing to constitute the X-ray detector 15.

In this solid state image sensing section 13, the X-ray detecting layer is made of a cesium iodide (CsI) layer and incident X-rays emit their energy in the CsI layer, are converted to fluorescent light and the converted light is guided to a photodiode on the TFT transistor circuit through a CsI columnar crystal structure. In the photodiode, light is converted to electric charge and the converted charge is stored in a capacitor and read by a reading circuit of the TFT transistor circuit as an electric signal. This photodiode corresponds to 1 pixel and the electric signal is read for each of pixels arranged in a matrix form. Furthermore, this reading circuit allows non-destructive reading and the control circuit 143 can select destructive reading or non-destructive reading. However, when the solid state image sensing element incapable of non-destructive reading is ready for receiving light, electric charge according to the amount of incident light is stored in each pixel of the element, but when this stored electric charge is taken out of the element as an electric signal, there is no more electric charge inside the element. For this reason, once the electric signal is read, it is only possible to store and read the electric charge received from the time at which the signal is read onward. On the other hand, in the case of the solid state image sensing element capable of non-destructive reading, even if the stored electric charge is taken out of the element as an electric signal, the electric charge inside the element is not destroyed. Therefore, it is possible not only to obtain an output which is proportional to the amount of charge of each pixel in the middle of storage but also to continue the charge storing operation.

When FIG. 1 is referenced again, the digital image data output from the X-ray detector 15 is sent to a signal processing device 7 and recorded in an image memory 71. The signal processing device 7 is connected to an image display monitor 8 and in addition to the memory 71, the signal processing device 7 also includes a calculator 72 which performs calculations such as additions or subtractions on the image data, a gray scale adjusting device 73 which adjusts the gray scale of the image displayed on the monitor 8 and an image process designating device 74. The image process designating device 74 controls the image memory 71, the calculator 72 and gray scale adjusting device 73 based on a command from the image taking control device 3.

The X-ray digital tomographic image taking apparatus of this embodiment having the above described configuration operates as shown below.

In preparation for image taking, in order to obtain a desired tomographic image for diagnosis, the operator sets the tomographic image taking condition from the image taking condition setting device 5. The principal conditions are X-ray irradiation conditions such as a tube voltage, tube current and X-ray irradiation time, image taking angle range and image taking count and an example thereof will be shown in FIG. 3. That is, suppose a range of 45° leftward and rightward, that is, a range of 90° centered on a plumb line G which passes through the center of the tomographic surface 21 is an image taking angle range, the point at which the X-ray tube 12 is located at position P1 is an image taking start point and the point at which the X-ray tube 12 is located at position P2n is an image taking end point. This range is further subdivided into four image taking ranges of approximately 22.5° each. Suppose the point at which the X-ray tube 12 is located at position P1 is the image taking start point, the range from this position P1 to position Pn/2 is a first image taking range, the range from position Pn/2+1 to position Pn is a second image taking range, the range from position Pn/n+1 to position P3n/2 is a third image taking range and the range from position P3n/2+1 to position P2n is a fourth image taking range.

Figure 3:
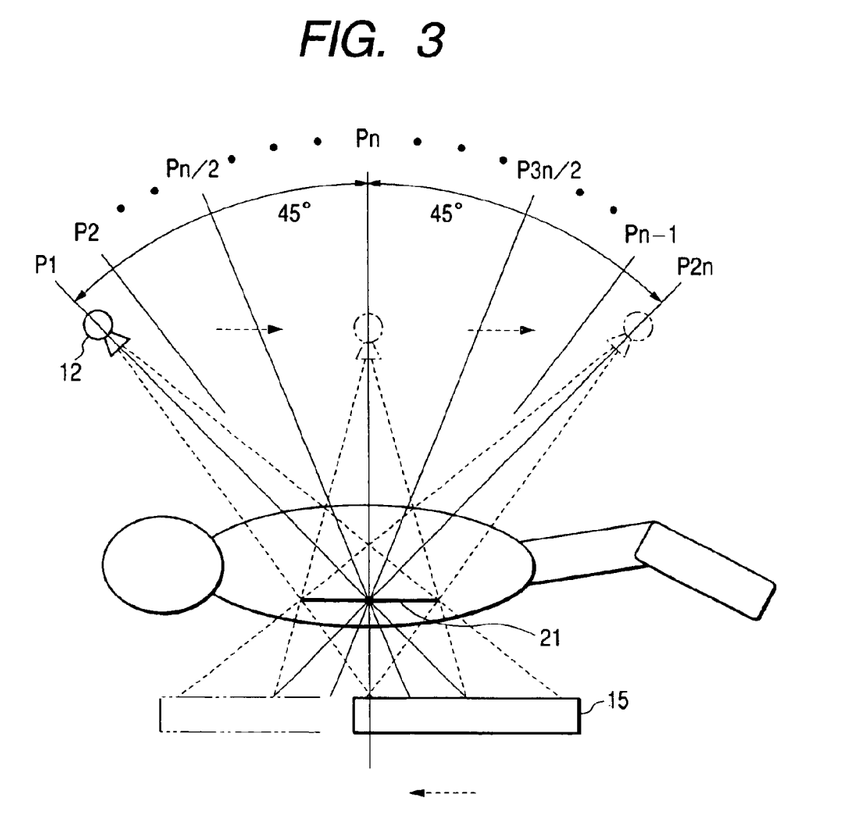
FIG. 3 is a schematic view of a tomographic image taking process.

In image taking of the subject in the above described image taking process, the setting is made in such a way that pulse X-rays are irradiated at the respective positions (P1, P2, ..., P2n−1, P2n) obtained by dividing the range from position P1 to position P2n into (2n−1) equal parts and 2n image takings are performed as a consequence. In this embodiment, the tube current I is set to I1, the X-ray irradiation time T is set to T1 and each condition is kept constant during 2n image takings. The tube voltage V is set to Vh (high voltage value) for the first and third image taking ranges and Vl (low voltage value) for the second and fourth image taking ranges and kept constant during the same image taking range.

Then, when the image taking start switch 31 is pressed and the signal is sent to the image taking control device 3, the image taking control device 3 sends a command necessary for image taking to the tomographic image taking stand 1, X-ray control device 4 and image taking drive section 14 and controls the operation of each unit. That is, when a control signal which controls a drive section (not shown) provided inside the tomographic image taking stand 1 is sent to the tomographic image taking stand 1, the X-ray tube 12 and X-ray detector 15 connected by means of the swing lever 16 start to move from the position shown in FIG. 1 in the direction shown by the dotted arrow.

Furthermore, when the X-ray irradiation condition and image taking start signal are sent to the X-ray control device 4, the X-ray control device 4 operates the high voltage generator 6 to cause the X-ray tube 12 to irradiate X-rays of the tube voltage Vh, tube current I1 and irradiation time T1 and irradiate pulse X-rays under the same X-ray irradiation condition at predetermined time interval t1 from then on. In the following explanations, changing the energy of X-rays is equivalent to changing the quality of X-rays. The change of the quality of X-rays is mainly achieved by changing tube voltage V.

Furthermore, when the image taking condition and image taking start signal are sent to the control circuit 143 in the image taking drive section 14, the control circuit 143 operates the TFT transistor circuit 132 every time irradiation of pulse X-rays ends and reads X-rays that have passed through the subject 2 as an electric signal, repeats the same operation at time interval t1 from then on to control so that X-rays are read as an electric signal. Here, with regard to reading of the electric signal corresponding to X-ray irradiation at time interval t1, control is performed in such a way that destructive reading is performed only when the X-ray tube 12 is located at the final image taking position in each image taking range from the first position to fourth position, that is, position Pn/2, position Pn, position P3n/2 and position P2n, and non-destructive reading is performed otherwise. Then, in response to 2n X-ray irradiations from the point at which the X-ray tube 12 is located at P1 to position P2n, electric signals corresponding to the 2n frames from A1 to A2n are read from one pixel to another.

Figure 4:
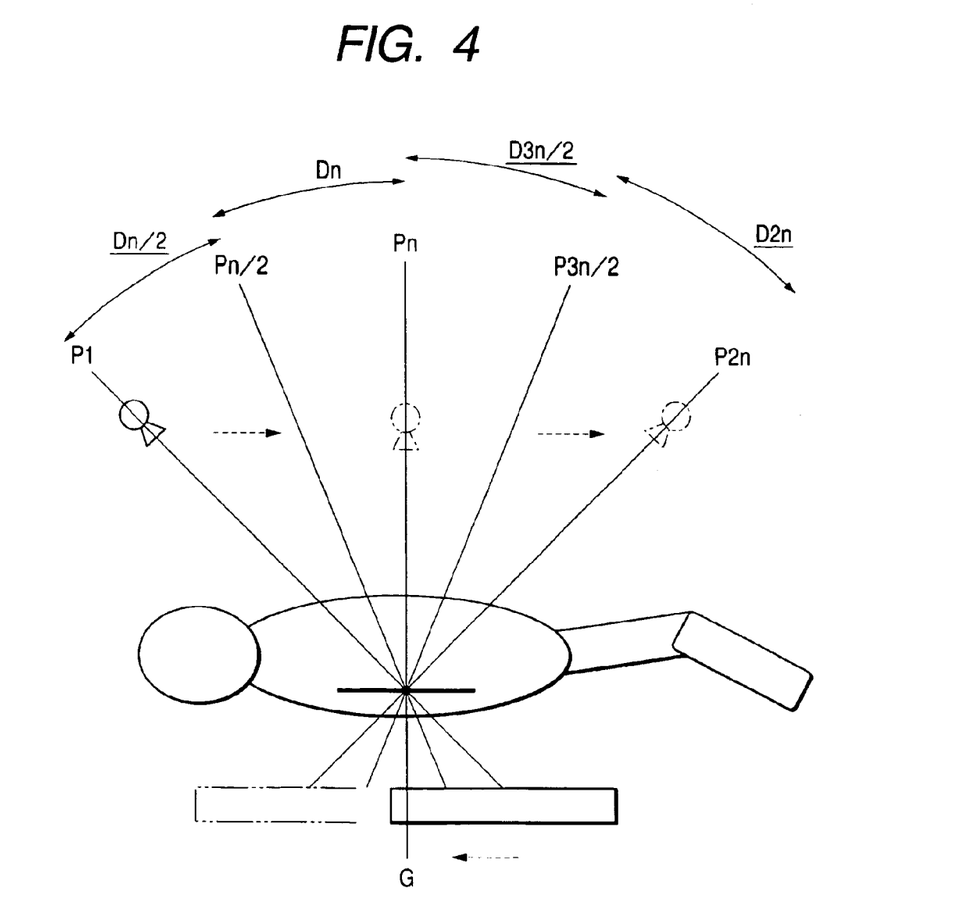
FIG. 4 illustrates a correlation between image data and image taking range.

The read electric signal is amplified according to the gain of the amplifier 141 which is preset to a default value and then converted to a digital signal by the A/D converter 142. Then, additional information such as frame numbers and image taking conditions, etc. is added sequentially for every 1-frame digital signal and digital image data corresponding to the 2n frames from D1 to D2n is generated finally. This digital image data is sent to and stored in the image memory 71 sequentially during tomographic image taking. However, the electric signal which is destructively read after the final image taking in the above described image taking range becomes the sum total of charge stored by individual image takings carried out from the start of image taking to the end of image taking of each image taking range. Therefore, as shown in FIG. 4, this digital image data becomes equivalent to the sum of the image data obtained by individual image takings in each image taking range. This is the operation of the image taking process.

Then, the operation of the image data processing step will be explained.

In preparation for image taking, the operator also sets the condition of reconstructing the tomographic image in addition to the tomographic image taking condition from the image taking condition setting device 5. In this embodiment, commands for calculating high voltage tomographic images from the first and third image taking ranges and low voltage tomographic images from the second and fourth image taking ranges based on the set tomographic image taking conditions, then carrying out weighted difference processing on these images and thereby reconstructing a dual energy subtraction tomographic image with only bones of the subject extracted and displaying are sent from the image taking control device 3 to the image process designating device 74, and the image process designating device 74 controls the image memory 71, calculator 72 and gray scale adjusting device 73 as follows.

Of the image data D1 to D2n corresponding to the 2n frames sent to and stored in the image memory 71, image data Dn/2, Dn, D3n/2 and D2n are sent to the calculator 72, where additions of [Dn/2+D3n/2] (=Dh) and [Dn+D2n] (=Dl) are performed and then these two image data Dh and Dl are resent to the image memory 71 and stored temporarily. Then, these two image data are resent to the calculator 72 and coefficients in the entire image data Dh of the high voltage tomographic image are multiplied (weighted) so that the concentration value of the soft tissue of the image data Dh of the high voltage tomographic image becomes equal to the concentration value of the soft tissue of the image data Dl of the low voltage tomographic image, then a difference between the image data of the weighted high voltage tomographic image and image data of the low voltage tomographic image is calculated. Through this difference processing, the soft tissue is erased and the image data of the tomographic image with only bones extracted is reconstructed. Then, this image data is sent to and stored in the image memory 71, sent to the monitor 8 through the gray scale adjusting device 73 and a tomographic image with bones of the subject extracted is displayed.

Furthermore, since the image data in each image taking range is read non-destructively, for example, difference data for each pixel of the image data acquired in the adjacent reading processes of the image taking process such as [D2n−D2n−1] and [Dn−Dn−1] become image data obtained by diagonal insertion or normal image taking at positions at which the X-ray tube 12 is located at positions P2n and Pn. When such reconstruction of image data is carried out between all image data acquired in the adjacent reading processes, it is possible to obtain data equivalent to the image data when all the image data after individual image takings is read destructively.

In a modification example of this embodiment, it is also possible to successively irradiate X-rays for each image taking range without using pulse X-rays.

Furthermore, after the final image taking in each image taking range an electric signal is read destructively, but it is also possible to read the electric signal non-destructively, then read it destructively, reset the charge stored in the solid state image sensing section and start image taking within the next image taking range.

Furthermore, instead of switching between the tube voltages, it is also possible to selectively place an X-ray filter for changing the energy of irradiated X-rays using filter replacing means disclosed in Japanese Patent Registration No. 2871053 which is a prior art between the X-ray tube and subject for each image taking range.

Then, another embodiment will be explained in association with the above described embodiment.

While the configuration of the X-ray digital tomographic image taking apparatus and the operation in the image data processing process are the same as those of the above described embodiment, the image taking process operates as follows.

In preparation for image taking, the same tomographic image taking condition as that of the above described embodiment is set from the image taking condition setting device 5. The principal conditions are X-ray irradiation conditions such as a tube voltage, tube current and X-ray irradiation time, image taking angle range and image taking count. When the image taking start switch 31 is pressed, the X-ray tube 12 and X-ray detector 15 start to move as in the case of the above described embodiment, the X-ray tube 12 irradiates pulse X-rays of a tube voltage Vh, tube current I1 and irradiation time T1 at predetermined time interval t1. Then, every time irradiation of pulse X-rays ends, X-rays that have passed through the subject 2 are stored in a solid state image sensing section as charge for each pixel. However, in this embodiment, this charge is not read as an electric signal for individual image takings, but the charge is read destructively all together when the final image taking ends in each image taking range. That is, the read electric signal becomes the sum total of the charge stored in individual image takings carried out from the start to the end of the image taking in each image taking range. Therefore, the electric signals acquired are only four electric signals equivalent to An/2, An, A3n/2 and A2n acquired in the above described embodiment.

Then, these read electric signals are subjected to the same processing as that of the above described embodiment and digital image data corresponding to four frames of Dn/2, Dn, D3n/2 and D2n is finally generated. This is the operation in the image taking process. The image data processing process also operates in totally the same way as in the above described embodiment and the tomographic image with bones of the subject extracted is displayed on the monitor 8.

Then, a further embodiment will be explained.

Figure 5:
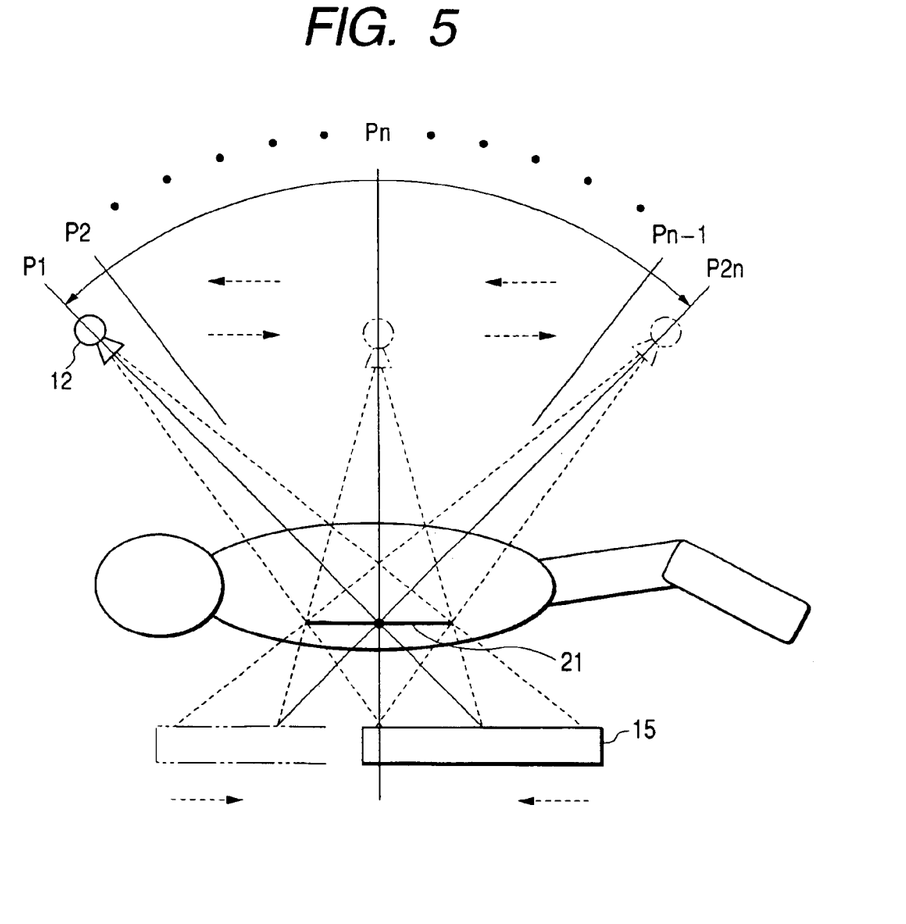
FIG. 5 is a schematic view of an image taking condition.

The configuration of the X-ray digital tomographic image taking apparatus is the same as the above described embodiment, but it operates based on the image taking condition shown in FIG. 5. That is, suppose a range of 45° leftward and rightward, that is, a range of 90° centered on a plumb line G which passes through the center of the tomographic surface 21 is an image taking angle range or the image taking range of the path to the turning point from the point at which the X-ray tube 12 is located at position P1 as an image taking start point through position Pn to the point at which the X-ray tube 12 is located at position P2n as an image taking end point. Furthermore, suppose the range from the point at which the X-ray tube 12 is located at position P2n as the image taking start point through position Pn to the point at which the X-ray tube 12 is located at position P1 as the image taking end point is the range of the path to the starting point.

In the above described process of taking an image of the subject, the setting is made in such a way that the subject is irradiated with pulse X-rays twice and images are taken at positions obtained by subdividing the range from position P1 to position P2n into (2n−1) equal parts (P1, P2, . . . , P2n−1, P2n) and as a result, images are taken 2n×2 (=4n) times. In this embodiment, the tube current I is set to I2, the X-ray irradiation time T is set to T2 and each condition is kept constant during 4n image takings. The tube voltage V is set to Vh (high voltage value) for the image taking range of the path to the turning point and Vl (low voltage value) for the image taking range of the path to the starting point and kept constant during image taking within the same range.

When the image taking start switch 31 is pressed, the movements of the X-ray tube 12 and X-ray detector 15 are started, the X-ray tube 12 irradiates pulse X-rays of the tube voltage Vh, tube current I2 and irradiation time T2 at predetermined time interval of t2. Then, every time irradiation of pulse X-rays ends, X-rays that have passed through the subject 2 are stored as charge for every pixel in the solid state image sensing section and control is performed in such a way that destructive reading is carried out only when images are taken when the X-ray tube 12 is at the final image taking position in both the image taking ranges of the path to the turning point and the path to the starting point, that is, at position P2n and position P1 and non-destructive reading is carried out otherwise.

Figure 6:
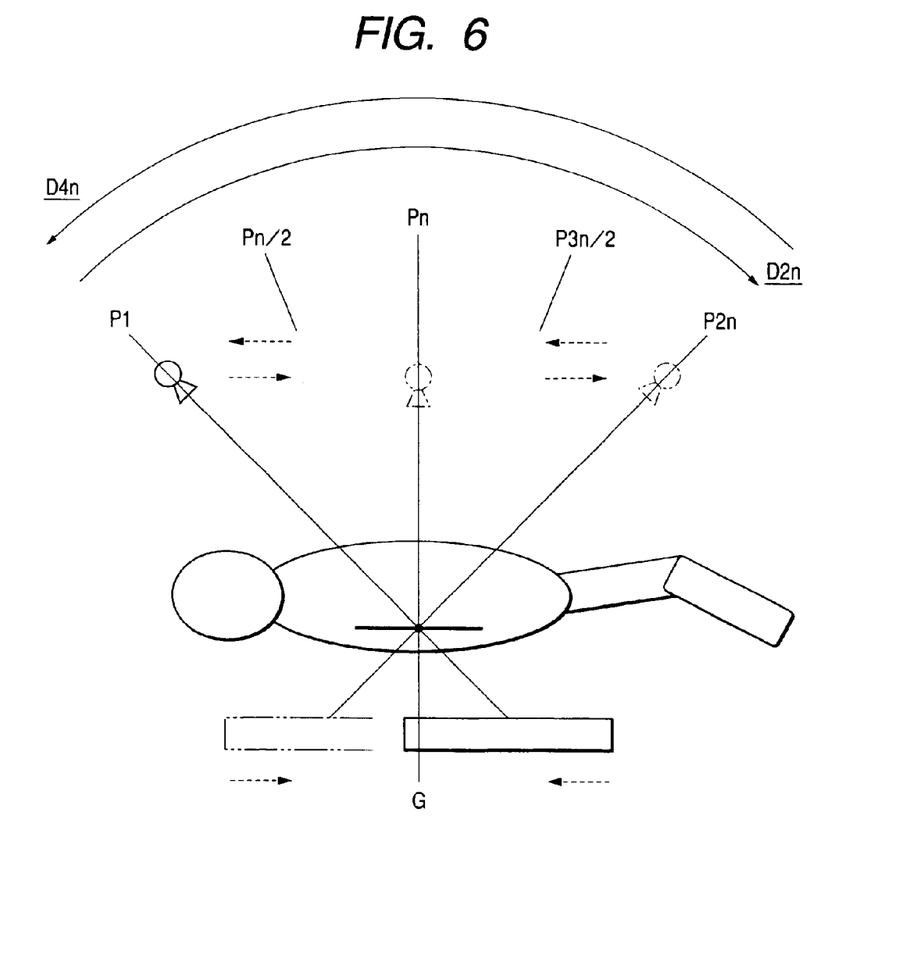
FIG. 6 illustrates a correlation between image data and image taking range.

Then, in response to 4n X-ray irradiations after the X-ray tube 12 moves from the point P1 through position P2n until it returns to position P1 again, electric signals corresponding to the 4n frames from A1 to A4n are read for each pixel. These read electric signals are processed in the same way as the above described embodiment, digital image data corresponding to the 4n frames from D1 to D2n are created finally and sent to and stored in the image memory 71. Then, the electric signal read destructively after the final image taking of the above described both image taking ranges becomes the sum total of charge stored by individual image takings carried out from the start to end of image taking in each image taking range. Therefore, as shown in FIG. 6, this digital image data is equivalent to the sum of the image data obtained by individual image takings in each image taking range. This is the operation in the image taking process.

The basic flow of image data in the image data processing process is the same as that of the above described embodiment, but the image data D2n and D4n become a high voltage tomographic image and low voltage tomographic image and by applying weighted difference processing to these images causes a dual energy subtraction tomographic image with only bones of the subject extracted to be displayed on the monitor 8.

Furthermore, as explained above, the number of sections with different X-ray energy levels into which the tomographic image taking process is divided is not limited to 4 or 2 in the above described embodiments.

It goes without saying that the object of the present invention can also be achieved by supplying a storage medium which records software program codes for implementing the functions of the above described embodiments to the system or apparatus and causing a computer (or CPU or MPU) of the system or apparatus to read and execute the program codes stored in the storage medium.

In this case, the program codes read from the storage medium themselves implement the functions of the above described embodiments and the program codes themselves and the storage medium that stores the program codes constitute the present invention.

As the recording medium to supply the program codes, for example, a flexible disk, hard disk, optical disk, magneto-optical disk, CD-ROM, CD-R, magnetic tape, non-volatile memory card and ROM, etc., can be used.

It goes without saying that the present invention includes not only the case where the functions of the above described embodiments are realized by the computer executing the read program codes but also the case where the OS (operating system) which is operating on the computer executes part or whole of actual processing based on the instructions of the program codes and realizes the functions of the above described embodiments through the processing.

Furthermore, it goes without saying that the present invention also includes the case where after the program codes read from the storage medium are written to the memory provided for a function expansion board inserted in the computer or a function expansion unit connected to the computer, the CPU, etc., provided on the function expansion board or function expansion unit executes part or whole of actual processing based on the instructions of the program codes and the functions of the above described embodiments are realized through the processing.

As described above, the X-ray digital tomographic image taking apparatus according to the present invention can reduce the tube voltage, the number of times filters are switched, and can thereby extend the service life of the tube, improve the diagnostic efficiency and realize an inexpensive filter switching apparatus.

Furthermore, the X-ray digital tomographic image taking apparatus according to the present invention can reduce the number of calculations for reconstruction of a tomographic image.

(Other Embodiment)

Note that the present invention may be applied to either a system constituted by a plurality of apparatuses (e.g., an image processing apparatuses, interfaces, radiographic apparatuses, X-ray generation apparatuses, and the like) or an arrangement that integrates an image processing apparatus and a radiographic apparatus, or the like.

The present invention is not limited to the above embodiments and various changes and modifications can be made within the spirit and scope of the present invention. Therefore to apprise the public of the scope of the present invention, the following claims are made.

What is claimed is:

1. An X-ray digital tomographic image taking apparatus comprising:
   an X-ray generation unit for emitting X-rays;
   a first transfer unit for changing the emission direction of X-rays emitted by the X-ray generation unit and transferring the X-ray generation unit;
   a solid state image sensing unit consisting of a plurality of solid state image sensing elements for converting X-rays to electric signals;
   a second transfer unit for transferring the solid state image sensing unit; and
   a control unit for controlling the first transfer unit and second transfer unit so that X-rays emitted from said X-ray generation unit are emitted to predetermined coordinates on the photoreceiving surface of said solid state image sensing unit, and controlling the emissions of the X-ray generation unit and the drive of the solid state image sensing unit,
   wherein said control unit divides the course along which said X-ray generation unit or solid state image sensing unit is moving into a plurality of sections and controls said X-ray generation unit so that the quality of said X-rays differs between neighboring sections.

2. The apparatus according to claim 1, wherein said control means divides the course along which said X-ray generation unit or solid state image sensing unit is moving into a plurality of sections and controls said X-ray generation unit so that the quality of said X-rays differs from one section to another and controls the drive of said solid state image sensing unit so that said solid state image sensing element stores charge while substantially keeping the amount of charge for a period during which said X-ray generation unit is repeating emissions a predetermined number of times or for each section.

3. The apparatus according to claim 1, wherein said control means divides the course along which said X-ray generation unit or solid state image sensing unit is moving into a plurality of sections and controls said X-ray generation unit so that the quality of said X-rays differs from one section to another, controls the drive of said solid state image sensing unit so that said solid state image sensing element stores charge while substantially keeping the amount of charge for a period during which said X-ray generation unit is repeating emissions a predetermined number of times or for each section and controls the drive of said solid state image sensing unit so that said solid state image sensing element discharges after a predetermined number of emissions or for said each section.

4. The apparatus according to claim 1, wherein the quality of said X-rays is changed by switching the tube voltage of said X-ray generation unit between a high voltage and low voltage.

5. The apparatus according to claim 1, wherein the X-ray digital tomographic image taking apparatus allows a plurality of types of X-ray filters for changing X-ray energy to be selected and placed between said X-ray generation unit and solid state image sensing unit, and comprises filter replacing means for replacing said X-ray filters, said controlling means changing the quality of X-rays by controlling said filter replacing means.

6. The apparatus according to claim 1, wherein said tomographic image taking apparatus comprises:
   an A/D conversion unit for A/D-converting the output of said solid state image sensing unit into image data; and
   a storing unit for saving the image data output from said A/D conversion unit at a predetermined image taking interval.

7. The apparatus according to claim 6, further comprising:
   calculating means for reconstructing the image data taken with the same quality out of the image data stored in said storage unit as a tomographic image of the quality; and
   subtracting means for carrying out a weighted subtraction on a plurality of tomographic images differing in quality which are reconstructed by said calculating means.

* * * * *